United States Patent [19]

Dobruskin

[11] Patent Number: 4,894,061

[45] Date of Patent: Jan. 16, 1990

[54] CONTAINER FOR AND METHOD OF PRESERVING AND INCREASING BACTERICIDAL PROPERTY OF POSITIVE SILVER IONS SOLUTIONS

[76] Inventor: Moisey Dobruskin, 483 Ocean Pkwy., Brooklyn, N.Y. 11218

[21] Appl. No.: 126,872

[22] Filed: Nov. 30, 1987

[51] Int. Cl.$^4$ .............................................. A61B 19/00
[52] U.S. Cl. ..................................... 604/403; 604/55; 361/212; 215/12.1; 215/12.2
[58] Field of Search .......................... 604/55, 265, 403; 215/12.1, 12.2; 361/212

[56] References Cited

U.S. PATENT DOCUMENTS

| 922,174 | 5/1909 | Lyman | 215/12.2 |
| 3,940,001 | 2/1976 | Haefner et al. | 215/12.2 X |

Primary Examiner—Allen M. Ostrager
Attorney, Agent, or Firm—Ilya Zborovsky

[57] ABSTRACT

Positive silver ions solution is accommodated in a container which is provided with means for maintaining the electrical charge of the solution or activating the solution, so as to preserve or to enhance the bactericidal property of the solution.

17 Claims, 3 Drawing Sheets

CONTAINER FOR AND METHOD OF PRESERVING AND INCREASING BACTERICIDAL PROPERTY OF POSITIVE SILVER IONS SOLUTIONS

BACKGROUND OF THE INVENTION

The present invention relates to a container for and a method of preserving and increasing bactericidal property of positive silver ions solutions.

It is known that anode-dilluted silver produced by electrolysis possesses strong bactericidal property. Under the action of electric current, atom of silver loses its electron and becomes a positively charged ion of silver or silver cation. The solution of silver ions in water is instable, even if it is accommodated in a container of plastic material. The solution of silver cations has its own electric field and therefore electric energy. Bactericidal strength or power of this solution is equal to the quantity of silver cations times the electric charge or quantity of electricity. It is also known that metal silver has only bacteristatic action. Therefore if silver cations lose their electric charge, they are converted into metal silver and lose their bactericidal property or action.

When the cation solution is accommodated in a container, its electric field polarizes the wall of the container and forms in wall polar molecules or dipoles. All dipoles are aligned along the electric field power lines and form a system. Thereby the silver cation solution loses a part of its energy to the process of polarization and to maintenance of the polarization. Additional loses occur to maintain its own free energy, to maintain its own electric field, amd also because of interaction with the electromagnetic fields of the Earth, atmosphere, cosmos. Therefore, immediately after preparation of silver cations solutions, they start changing and gradually lose their positive electric charge. The quantity of silver in the solution does not change, however its bactericidal action decreases and eventually disappears.

SUMMARY OF THE INVENTION

Accordingly, it is an object of the present invention to provide a container and a method which avoid the disadvantages of the prior art.

In keeping with these objects and with others which will become apparent hereinafter, one feature of the present invention resides, briefly stated, in a container for accommodating silver cations solutions, which is provided with an additional layer at least preventing electric charge loses of the solution.

Another feature of the present invention is to provide a method in accordance with which a container accommodating a silver cations solution is provided with a layer which at least prevents loses of electric charge of the solution.

When the container is designed and the method is performed in accordance with the present invention, they avoid the above explained disadvantages of the prior art.

The novel features of the present invention are set forth in particular in the appended claims. The invention itself, however, both as to its construction and its method of operation, will be best understood from the following description of preferred embodiments which is accompanied by the following drawings.

DESCRIPTION OF PREFERRED EMBODIMENTS

Figure 1:
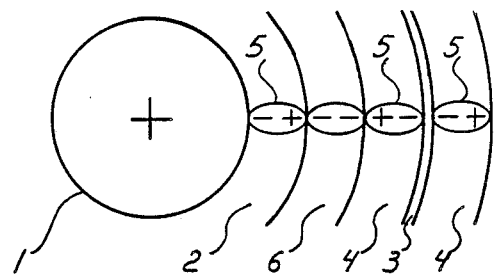
FIG. 1 is a view showing a container which accommodates a silver cations solution and provided with means for preventing loses of its electrical charge.
Figure 2:
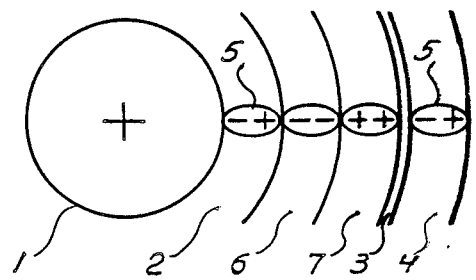
FIGS. 2-5 are views showing the container in accordance with further embodiments of the loses preventing means for the solution.

FIG. 1 shows a cross section of a container for accommodating silver cations solution which is identified with reference numeral 1. The wall of the container is composed of several layers. An inner layer 2 is formed of a dielectric such as for example polyethelene. This layer directly separates the solution from all other layer so as to form a phase separating structure. Molecules of the layer 2 are polarized from the outer side by the electrostatic field of a layer 6 and from the inner side by the field of the solution of silver cations 1. The polarized molecules of dipoles 5 of the layer 2 are oriented in a certain fashion. The layer 6 is a dielectric which during its manufacture is impregnated with negative static electricity. In the shown embodiment the electrostatic energy of the layer 6 is transformed into energy of charging of the silver cations solution by the induction process. The layer 6 is a generator of energy. A layer 4 is an insulator and can be composed of polyesther with polarized and spacially oriented molecules. A layer 3 is formed as a Faraday cage or a metal casing which screens or protects the whole container from the action of external electromagnetic fields, electrostatic charges, radiation, light, heat etc.

Figure 5:
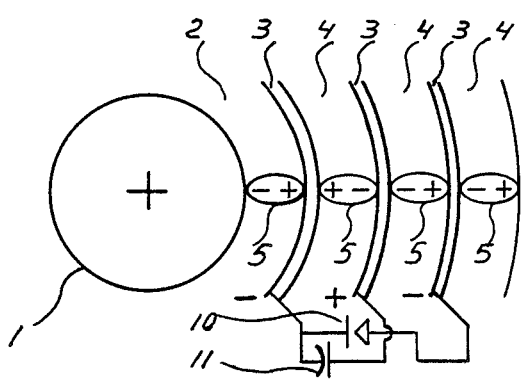

The wall of the container shown in FIG. 5 is composed of five layers. Layers 6 and 7 are energy generating layers. The layer 7 is formed from a dielectric impregnated during its manufacture with positive static electricity. In this construction the electrostatic energies of the layers 6 and 7 are added and doubled. The energy of these layers induce the solution of silver cations. The layers 6 and 7 are thin ionexchange membranes on the basis of high molecular compositions which possess positively or negatively charged fixed ions.

Figure 3:
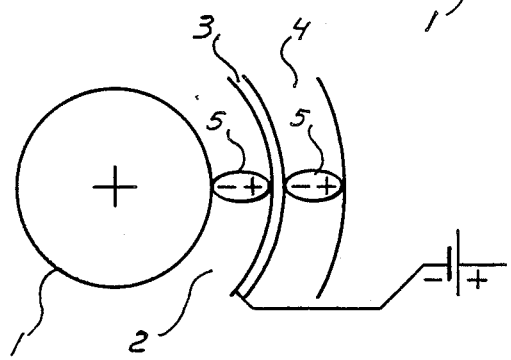

The wall of the container shown in FIG. 3 is composed of three layers. The Faraday cage here is supplied with a static energy from a battery 8. In this construction the silver cations are additionally charged by induction.

Figure 4:
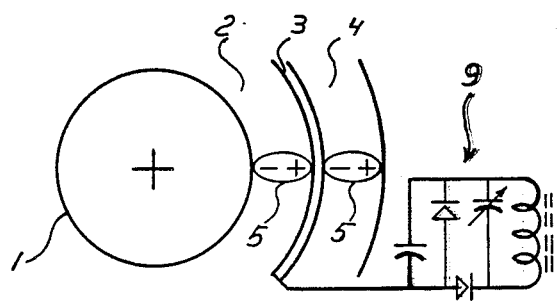

The wall of container of FIG. 4 has three layers, similarly to FIG. 3. The screen layer 3 here is supplied with energy of an external electromagnetic field from a convertor 9. The circuit of the convertor 9 is tuned to a nearby powerful radio station.

The container of FIG. 5 has seven layers. Three of these layers are formed as a Faraday cage. They form screens which not only protect the construction from the external fields, but also accummulate the energy of external fields. With the aid of a diode 10 and condensor 11 this energy is concentrated on the inner screen 3, and from there is induced into the solution of silver cations.

The containers shown in FIGS. 6–12 can have constructions which can correspond to any of the constructions of FIGS. 1–5. However, here there are means for extra activation of the silver cation solutions before its use.

Figure 6:
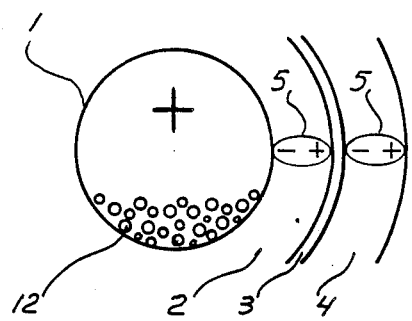
FIG. 6 is a view showing a container which accommodates a silver cations solution and provided with means for increasing electrical charge of the solution.

The container of FIG. 6 with the solution of silver cations has small spheres from fluoroplastic, polyethelene etc. which are freely accommodated in the container. Before use, the container must be shaken. Under the action of friction, the spheres are electrified in the solution. The silver cation solution receives powerful additional positive charge required for superactivation.

Figure 7:
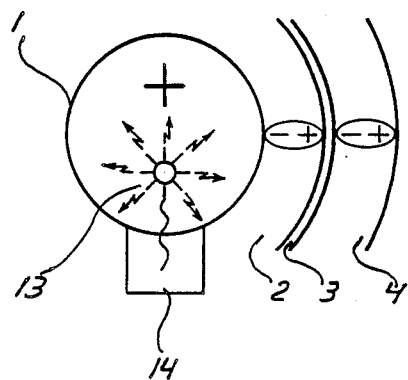
FIGS. 7-13 are views showing the container in accordance with further embodiments of the electrical charge increasing means in accordance with the present invention.

The container in FIG. 7 has a piezo electric convertor 14 of mechanical energy into electrostatic energy, for example with potential of 5–10 kV. It is located outside of the container. Inside the container in the silver cations solution, there are needles for flowing off the electrical charges into the solution to provide the activation. The piezo electric convertor is actuated manually by a user.

Figure 8:
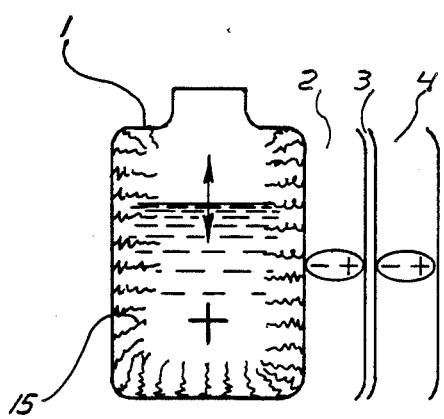

The container of FIG. 8 is provided on the inner surface of the layer 2 with a plurality of hairs and spirals composed of readily electrifyable plastic. During shaking of the container, the silver ions solution rubs against the hairs and spirals and is strongly electrified, to obtain additional electrical charges.

Figure 9:
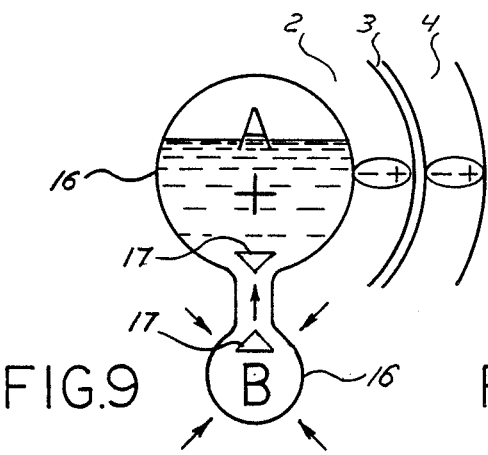
Figure 10:
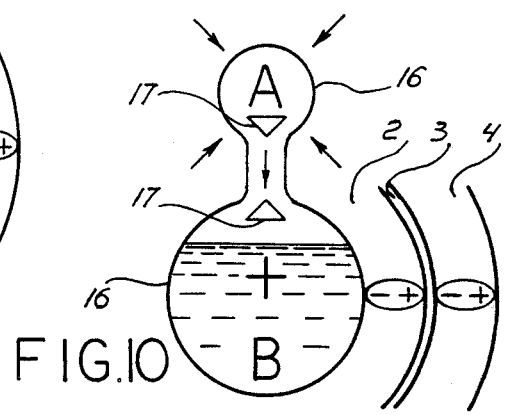

The containers of FIGS. 9 and 10 each have two spherical members A and B with elastic walls 16 with a construction similar to the constructions of FIGS. 1–5. The spherical members are connected with one another by a thin pipe with Faradey cones of readily electrifyable plastic at each end. During alternating squeezing the spherical members and thereby pumping the silver cation solution, powerful electrifying of the solution is produced. The electrifying takes place during striking of the solution against the cones and its atomization, resulting in the activation of the solution.

Figure 11:
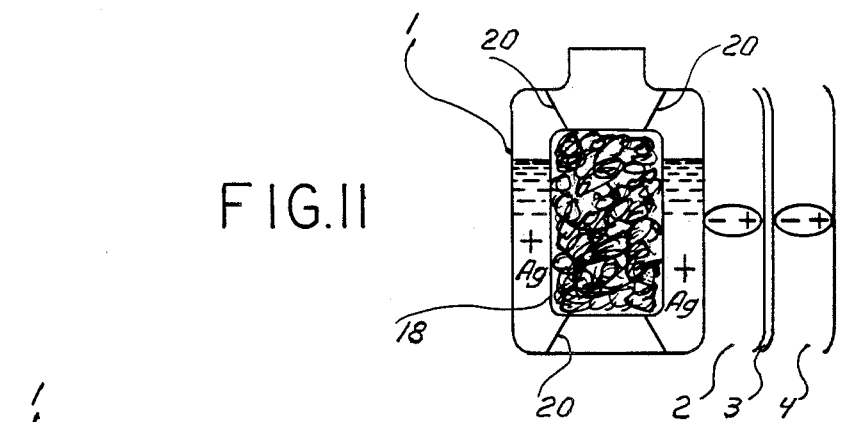

The container with silver cations solution shown in FIG. 11 has in it a hermetically closed plastic pack with a thermogenerator. The walls of the pack and the container are elastic and interconnected as identified with reference numeral 20. When the container is squeezed, the solution is electrified from friction, and simultaneously the solution is heated by the thermogenerator which is formed as known.

Figure 12:
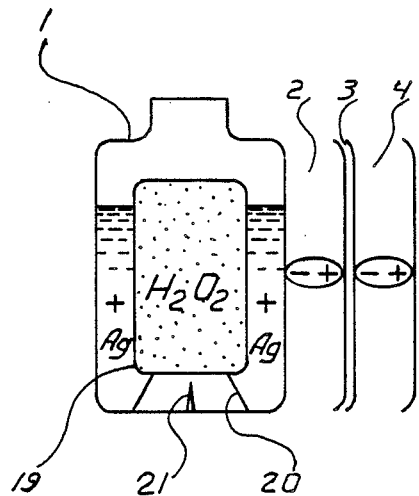

In the container of FIG. 12 there is a hermetically closed pack with hydrogen peroxide 19 and a perforating needle 21. The container and the pack are interconnected at 20. During squeezing of the container the needle 21 pierces the pack 19 and the hydrogen peroxide is mixed with the silver cations solution. During this process, free oxygen action is added to the solution and its bactericidal effect is increased.

Figure 13:
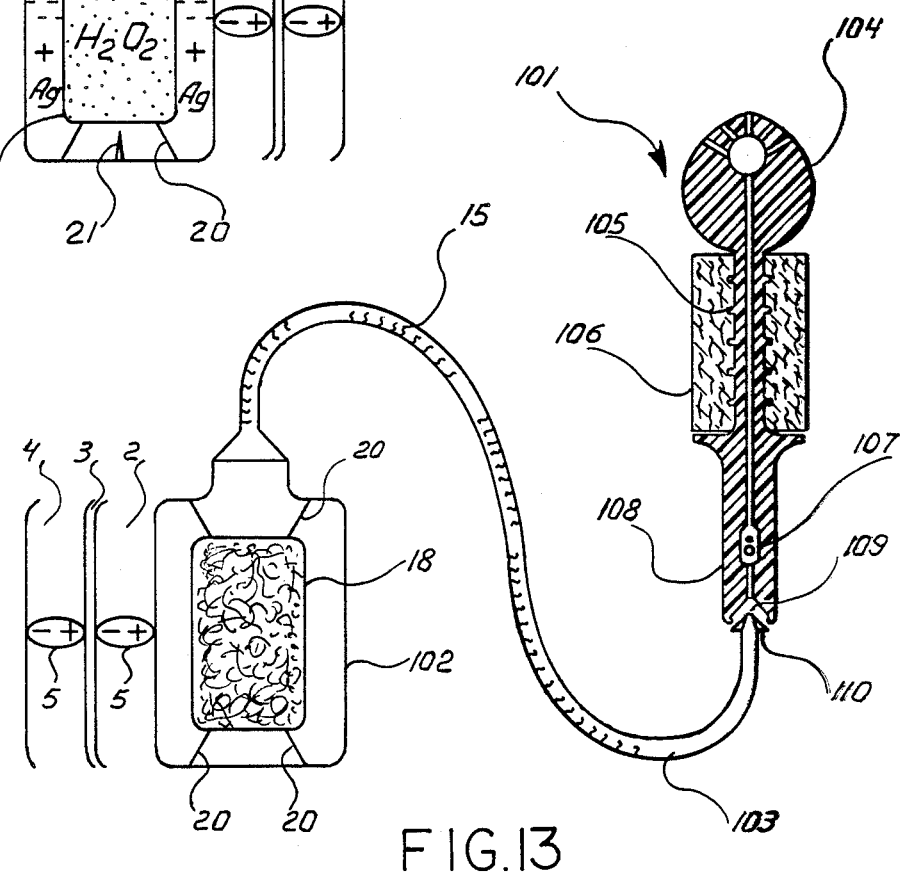

In FIG. 13 an elastic container 102 is formed as one of the containers shown in FIGS. 1–5. It has a hermetic thermogenerator 18. The container is connected by a pipe 103 with a special attachment 101 for desinfection of a vagina. The pipe 103 is provided with hairs and spirals which are electrified during flowing of the solution therethrough under the action of friction and give their static electricity to the solution. The attachement is provided with a condensing absorbing tampon 106 which swells under the action of liquid and retains the solution in the vagina during a required time.

The attachement has a directing head nozzle 104 with a shaft 105 with a conical surface 109, with which a nozzle 110 of the pipe 103 cooperates. An inflow valve 107 is located in the handle 108. The attachement is inserted into vagine, the solution is supplied into and discharged from the head nozzle 104 through narrow passages, while the tampon swells and seals the vagina.

The layers around the container can be of different thicknesses, for example between 0.1 and 1 mm.

The invention is not limited to the details shown since various modifications and structural changes are possible without departing in any way from the spirit of the present invention.

What is claimed and desired to be protected by Letters Patent is set forth in particular in the appended claims:

1. A container for preserving bactericidal property of positive silver ions solutions, comprising
   a wall bounding an inner chamber for accommodating a positive silver ions solution; and
   means for supplying additional energy to the positive silver ions solution so as to prevent decrease of electric charge of the positive silver ions solution.

2. A container as defined in claim 1, wherein said means includes a layer which contains a negative electric charge.

3. A container as defined in claim 1, wherein said means includes a layer which is formed as a Faraday cage, and an electrical source connected with said Faraday cage and supplying energy thereto.

4. A container as defined in claim 1, wherein said means includes a layer which forms a Faraday cage, and means for converting energy of external electromagnetic field and supplying the same to said Faraday cage.

5. A container as defined in claim 1, wherein said means includes a layer which is formed as a Faraday cage, and means for accumulating energy of external electromagnetic field in said Faraday cage.

6. A container as defined in claim 1, wherein said means includes a plurality of small bodies which are freely accommodated in the solution and electrifyable upon shaking the container.

7. A container as defined in claim 1, wherein said means includes a piezo electric convertor arranged to convert mechanical energy applied by a user to said wall into electrostatic energy.

8. A container as defined in claim 1, wherein said means includes a plurality of small formations fixed to said wall and electrifyable during shaking of the container.

9. A container as defined in claim 1, wherein said wall forms two container portions which communicate with one another and are squeezable for pumping the solution from one container portion to the other with electryfying the solution, so as to form said means.

10. A container as defined in claim 1, wherein said means includes a thermogenerator for heating the solution.

11. A container as defined in claim 1, wherein said means includes a hydrogen peroxide pack arranged inside said wall and piercable so as to release the hydrogen peroxide into the solution.

12. A container as defined in claim 1, and further comprising an attachement communicating with said chamber of said wall and having a nozzle head arranged to be inserted into a vagina for supplying into the latter the solution from said chamber, and a swellable tampon arranged to swell by a liquid and to seal the vagina.

13. A container as defined in claim 12, and further comprising a communicating pipe which connects said chamber with said head and is provided with means for activating the solution during its flow throigh said pipe from said chamber to said head.

14. A container as defined in claim 1, wherein said means includes a layer which contains a positive electric charge.

15. A container for preserving bactericidal property of positive silver ions solutions, comprising
   a wall bounding an inner chamber for accommodating a positive silver ions solution; and
   means for supplying additional energy to the positive silver ions solution so as to prevent decrease of electric charge of the positive silver ions solution accommodated in said inner chamber, said means including a layer associated with said wall and electrically charged so as to additionally charge the positive silver ions solution through said wall.

16. A container for preserving bactericidal property of positive ions solution, comprising
   a wall bounding a chamber for accommodating a positive silver ions solution; and
   means for supplying additional energy to the positive silver ions solution so as to prevent decrease of electric charge of the positive silver ions solution accommodated in said inner chamber, said means including a plurality of bodies accommodated in said inner chamber and electrically chargeable so as to additionally charge the positive silver ions solution in said inner chamber.

17. A method of at least preserving bactericidal property of positive silver ions solutions, comprising the steps of
   accommodating silver ions solutions in a container; and
   supplying additional energy to the positive silver ions solution so as to prevent decrease of electric charge of the positive ions solution.

* * * * *